US00PP12042P2

(12) United States Plant Patent
Fruehwirth

(10) Patent No.: US PP12,042 P2
(45) Date of Patent: Aug. 7, 2001

(54) POINSETTIA PLANT NAMED 'WINRED'

(75) Inventor: Franz Fruehwirth, Encinitas, CA (US)

(73) Assignee: Paul Ecke Ranch, Inc., Encinitas, CA (US)

( * ) Notice: Subject to any disclaimer, the term of this patent is extended or adjusted under 35 U.S.C. 154(b) by 0 days.

(21) Appl. No.: 09/431,243

(22) Filed: Nov. 1, 1999

(51) Int. Cl.[7] ..... A01H 5/00
(52) U.S. Cl. ..... Plt./307

(58) Field of Search ..... Plt./307, 306

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Winred', characterized by its incurved and curled red bracts; response time about 10 weeks; thick, strong and stiff lateral branches; very dark green leaves with thick red purple petioles; tall and upright plant habit; and good postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Winred'.

The new cultivar is a product of a planned breeding program conducted by the Inventor in Encinitas, Calif. The objective of the program is to create new Poinsettia cultivars having interesting bract and leaf display, color and form; strong and freely branching stems; and good post-production longevity.

The new cultivar originated from a cross made by the Inventor of the proprietary selection identified as M-18, as the female, or seed parent, with the proprietary selection identified as F-14, as the male, or pollen parent.

The cultivar Winred was discovered and selected by the Inventor as a flowering plant within the progeny of the stated cross in a controlled environment in Encinitas, Calif. in December, 1994.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Winred'. These characteristics in combination distinguish 'Winred' as a new and distinct cultivar:

1. Incurved and curled red bracts.
2. Response time about 10 weeks.
3. Thick, strong and stiff lateral branches.
4. Very dark green leaves with thick red purple petioles.
5. Tall and upright plant habit.
6. Good postproduction longevity.

In side-by-side comparisons conducted in Encinitas, Calif., plants of the new Poinsettia have a darker leaf and bract color than plants of the female parent, the selection M-18. Compared to plants of the male parent, the selection F-14, which has smooth bracts and leaves, plants of the new Poinsettia have incurved and curled bracts and leaves.

Plants of the new Poinsettia can be compared to plants of the cultivar Windark, disclosed in U.S. Plant Patent application Ser. No. 09/087,917. However, in side-by-side comparisons conducted in Encinitas, Calif., plants of the new Poinsettia differed from plants of 'Windark' in the following characteristics:

1. Plants of the new Poinsettia are taller than plants of 'Windark'.
2. Plants of the new Poinsettia are not as freely branching as plants of 'Windark'.
3. Plants of the new Poinsettia have stiffer stems than plants of 'Windark'.
4. Plants of the new Poinsettia have more and larger leaves than plants of 'Windark'.
5. Plants of the new Poinsettia have larger and taller (thicker) inflorescences than plants of 'Windark'.
6. Flower bract color of the new Poinsettia is slightly lighter than flower bract color of 'Windark'.
7. Plants of the new Poinsettia flower later than plants of 'Windark'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Winred'.

The photograph at the bottom top of the first sheet comprises a top perspective view of a typical plant of 'Winred'.

The photograph at the top of the second sheet comprises a top perspective view of typical inflorescences of 'Winred' (left) and 'Windark' (right).

The photograph at the bottom of the second sheet is a close-up view of typical bracts and leaves of 'Winred' (left) and 'Windark' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. Both the photographic illustrations and the following observations and measurements describe about 18 week old plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Winred'.

Parentage:

*Female parent.*—Proprietary selection of *Euphorbia pulcherrima* Willd. identified as M-18.

*Male parent.*—Proprietary selection of *Euphorbia pulcherrima* Willd. identified as F-14.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Freely branching, becoming fibrous with development.

Plant description:

*Plant form.*—Narrow inverted triangle.

*Growth habit.*—Tall and very upright. Not freely branching. Moderately vigorous.

*Plant height.*—About 30 cm.

*Plant spread.*—32 cm.

*Crop time.*—From unrooted cuttings to a flowering plant in a 16-cm container, about 18 weeks are required.

*Stem description.*—Appearance: Thick, strong and stiff. Number of lateral branches: About three lateral branches are formed after removal of the terminal apex. Lateral branch length: About 24 cm. Internode length: About 2.25 cm. Stem color: 146A.

*Foliage description.*—Arrangement: Alternate. Appearance: Leaves incurved toward stem; puckered and curled. Quantity of leaves per lateral branch: About 12. Length: About 11 cm. Width: About 7 cm. Shape: Ovate; very occasionally rounded lobed. Apex: Acuminate. Base: Rounded acute. Margin: Entire. Texture: Smooth, dull; very sparse pubescence on lower surface. Color: Young foliage, upper surface: Darker than 147A. Young foliage, lower surface: 147A. Mature foliage, upper surface: Darker than 147A. Mature foliage, lower surface: 147A. Venation, upper surface: 146B. Venation, lower surface: 147C. Petiole: Length: About 2.25 cm. Diameter: About 4 mm; thick. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time is about 10 weeks.

*Quantity of inflorescences.*—One per lateral branch, usually about three per plant.

*Inflorescence size.*—Diameter: About 15 cm. Height (depth): About 7 cm.

*Flower bracts.*—Appearance: Bracts incurved toward stem; puckered and curled. Quantity of flower bracts per inflorescence: Usually about 26 bract per inflorescence. Length, largest bracts: About 7.5 cm. Width, largest bracts: About 9 cm. Shape: Ovate. Apex: Acuminate. Base: Acute. Margin: Entire. Texture: Smooth, velvety. Aspect: Curled. Color: Developing, upper surface: 45B. Developing, lower surface: 45C. Mature, upper surface: Slightly more crimson that 45A. Mature, lower surface: 53C.

*Cyathia.*—Quantity: Usually about 12 per corymb. Diameter of cyathia cluster: About 2.5 by 2.5 cm. Length: About 1.1 cm. Width: About 6 mm. Color: Immature: 144B. Mature: 144B to 144C. Peduncle: Length: About 4 mm. Aspect: Strong, erect. Color: 144C. Stamens: Stamen number: Numerous, typically more than 20 per cyathium. Anther length: About 1 mm. Anther shape: Oval. Anther color: 45C. Amount of pollen: Moderate. Pollen color: 7A. Pistils: No pistillate flowers observed. Nectary color: 14A. Nectary number: 1.

Disease resistance: Plants of the new Poinsettia have been observed to be resistant to Botrytis.

Postproduction longevity: Excellent; generally plants maintain good substance and bract color for about six to eight weeks under interior conditions.

It is claimed:

1. A new and distinct cultivar of Poinsettia plant named 'Winred', as illustrated and described.

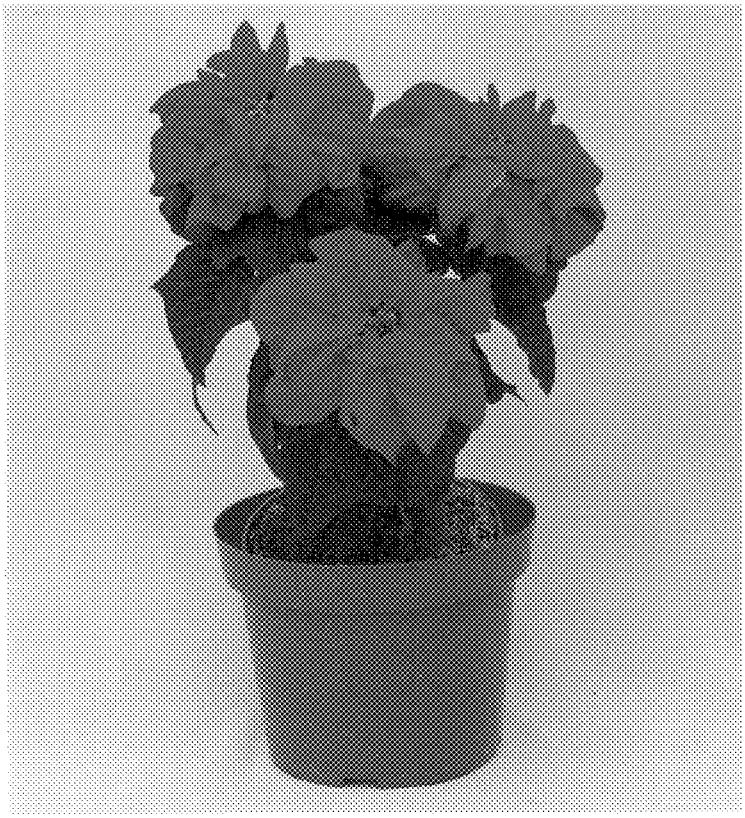
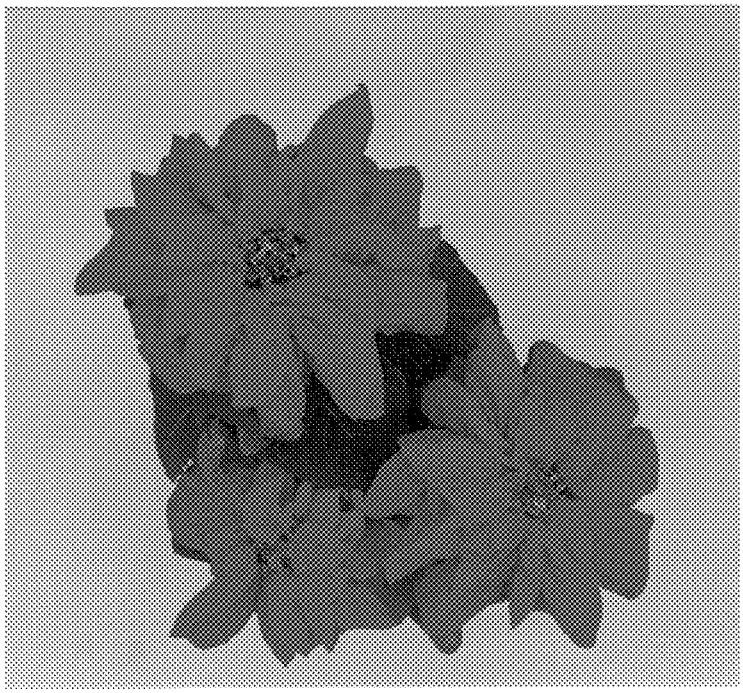

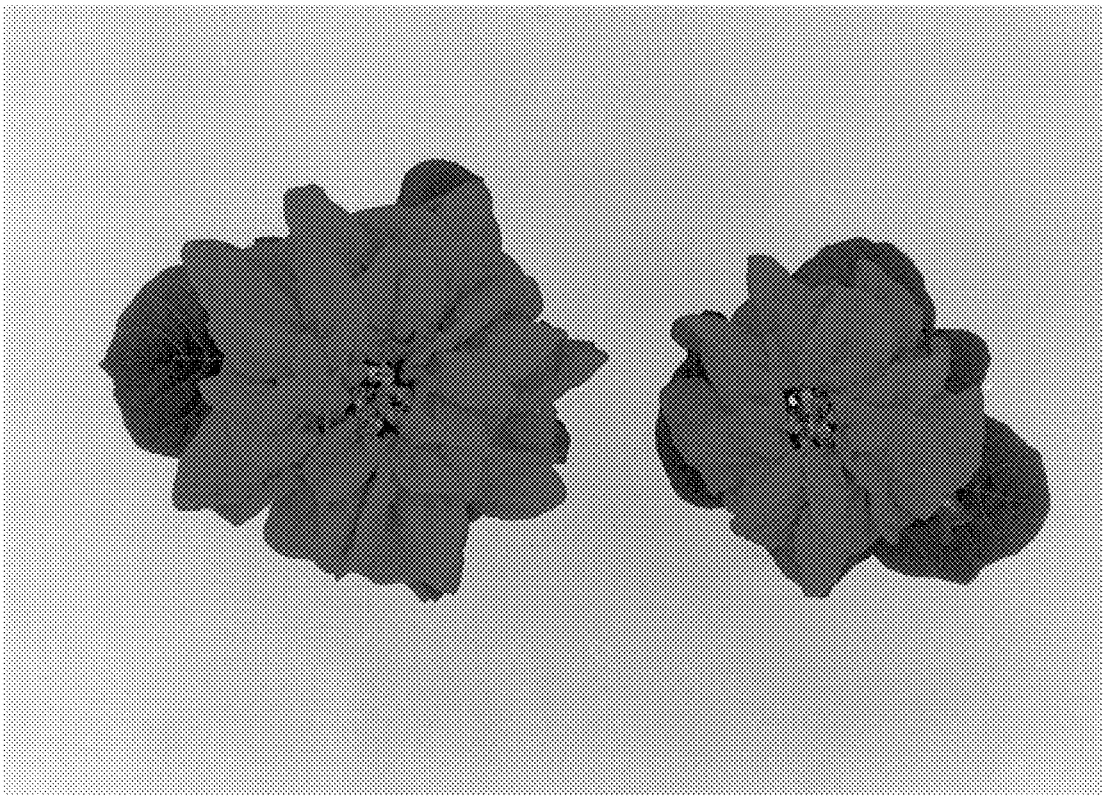
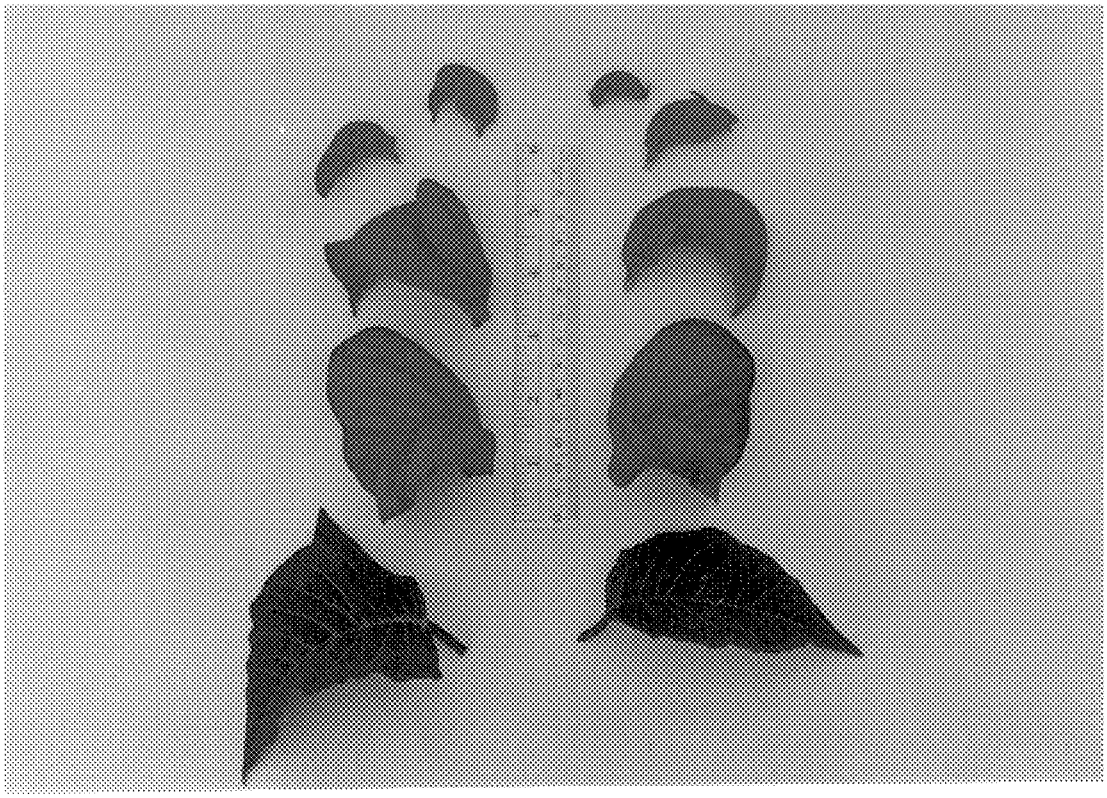

* * * * *